United States Patent [19]
Blosser et al.

[11] Patent Number: 4,739,173
[45] Date of Patent: Apr. 19, 1988

[54] COLLIMATOR APPARATUS AND METHOD

[75] Inventors: Gabe F. Blosser, Haslett; Emanuel B. Jemison, Lansing; Henry G. Blosser, East Lansing; Richard L. Maughan, Grosse Pointe Park, all of Mich.

[73] Assignee: Board of Trustees operating Michigan State University, East Lansing, Mich.

[21] Appl. No.: 896,730

[22] Filed: Aug. 15, 1986

Related U.S. Application Data

[63] Continuation-in-part of Ser. No. 850,486, Apr. 11, 1986.

[51] Int. Cl.⁴ .......................... G21K 1/02; G21K 1/04
[52] U.S. Cl. .................................. 250/505.1; 378/152
[58] Field of Search .................. 250/505.1, 363 SH; 378/147, 150, 152

[56]         References Cited
         U.S. PATENT DOCUMENTS

| | | | |
|---|---|---|---|
| 1,909,118 | 5/1933 | Raab | 378/152 |
| 3,543,384 | 12/1970 | Hansen | 250/505.1 |
| 4,053,808 | 10/1977 | Peacock | 378/152 |
| 4,158,779 | 6/1979 | Rommel et al. | 378/152 |
| 4,463,266 | 7/1984 | Brahme | 250/505.1 |
| 4,534,052 | 8/1985 | Milcamps | 378/152 |

FOREIGN PATENT DOCUMENTS

| | | | |
|---|---|---|---|
| 192300 | 11/1907 | Austria | 378/150 |
| 635489 | 3/1928 | France | 378/150 |
| 1258028 | 12/1971 | United Kingdom | 378/150 |

Primary Examiner—Bruce C. Anderson
Attorney, Agent, or Firm—Ian C. McLeod

[57]              ABSTRACT

A collimator apparatus (10 or 100) including one or more bundles of nested rods (11, 11a or 101 or 101a or 201) which define a surface (112, 112a) which interferes with a beam of radiation is described. The apparatus particularly uses coil spring (48) between and along the axis (a—a or c—c) of the rods which are compressed by blocks (13, 14, 13a and 14a or 103, 104, 103a and 104a) to lock the rods in position in holes in the blocks. The apparatus is particularly useful for shaping radiation beams for patient treatment.

22 Claims, 5 Drawing Sheets

COLLIMATOR APPARATUS AND METHOD

CROSS-REFERENCE TO RELATED APPLICATION

This application is a continuation-in-part of U.S. application Ser. No. 850,486, filed Apr. 11, 1986.

BACKGROUND OF THE INVENTION

(1) Summary of the Invention

The present invention relates to an improved collimator apparatus and method for focusing a beam from a radiation source. In particular the present invention relates to an apparatus which uses coil springs for locking nested rods together to define an opening for collimating the beam. Related U.S. application Ser. No. 850,486 describes a collimator apparatus which uses a clamping means to secure nested rods in position. This system works well; however, an improved means for moving and locking the rods to define the opening was needed.

(2) Prior Art

Collimator apparatus for focusing radiation are well known to the prior art. Most of these apparatus provide beams with a fixed cross-section which can be changed only by changing an insert which focuses the beam. This type of apparatus is cumbersome where the cross-section of the beam has to be repeatedly changed such as in patient treatment with radiation directed at a defined area of the body which is changed from patient to patient.

Variable collimator apparatus for radiation are also well known to the prior art. These apparatus provide a moveable interfering member in the beam. U.S. Pat. No. 4,463,266 to Brahme describes a collimator apparatus which uses wedge shaped slabs which move into the beam so as to define the beam. This apparatus is complicated and expensive to build because of the precision of the fit of the wedges relative to each other. Other prior art apparatus include camera or iris type lenses with uniformly change the diameter of the beam and thus are not suitable where the beam is to have an irregular cross-section. One prior art example is described in U.S. Pat. No. 4,534,052 to Milcamps. None of this prior art provides a means for rapidly and simply adjusting the beam cross-section non-uniformly.

OBJECTS

It is an object of the present invention to provide a collimator apparatus with a releasable clamping means which secures rods in blocks to define an irregular shaped opening for the radiation and which when released allows movement of the rods to a new position.

It is further an object of the present invention to provide a collimator apparatus with compressed coil spring means between nested rods for locking the rods together in a manner which insures locking of each rod to define an opening for shaping the cross-section of the radiation and which allows free movement of each rod when unlocked. Further it is an object of the present invention to provide a shaping means for moving the rods when they are unlocked to define the opening. Further still it is an object of the present invention to provide an apparatus which is simple and economical to construct and yet is reliable. Finally it is an object of the present invention to provide a method for using the collimator apparatus. These and other objects will become increasingly apparant by reference to the following description and the drawings.

IN THE DRAWINGS

FIG. 2 is a perspective view in partial section of the apparatus shown in FIG. 1 particularly showing two sets of blocks 13 and 14 and 13a and 14a journalling two bundles 12 and 12a of opposed rods 11 and 11a.

FIG. 3 is a partial section perspective view of one shaping member 40 shown in FIG. 1.

FIG. 4 is a partial section perspective view of two rods 11 and a spring 48 which acts to hold the rods 11 together when compressed, when there is a third rod over the spring (not shown).

FIG. 5 is an end cross-sectional view along line 5—5 of FIG. 2 showing the relationship of the springs 48 to the rods 11 such that each rod 11 is locked in position by a spring 48.

FIGS. 6 to 9 are schematic plan views of an apparatus 100 which shows the operation of the apparatus 10 of FIG. 1 and particularly showing a sequence of steps for defining an opening 111, wherein the bundles 102 and 102a of rods 101 and 101a are moved (FIGS. 6 and 7) and shaped (FIGS. 8 and 9) by the shaping members 110 and 110a.

GENERAL DESCRIPTION

The present invention relates to a collimator apparatus for producing a cross-sectionally shaped beam of radiation from a radiation source which comprises: support plate means having a central opening around a beam axis through which the beam of radiation can pass; a bundle of nested rods mounted adjacent the support plate means each rod being movable into the beam at an angle to the beam axis to interfere with the beam, the rods having first ends which together define a first surface for shaping the beam around the beam axis and opposite ends from the first ends of the rods; a holder means including spaced apart blocks mounted on the support plate, each block having axially aligned holes mounting the rods so that the first surface is defined and the beam is shaped by the first ends of the rod; releasable clamping means engaging the blocks to secure the rods together in the shape defined by the first ends of the rods.

The present invention particularly relates to a collimator apparatus for producing a cross-sectionally shaped beam of radiation from a radiation source which comprises: support plate means having a central opening around a beam axis through which the beam of radiation can pass; a bundle of nested rods mounted adjacent the support plate means each rod being movable into the beam at an angle to the beam axis to interfere with the beam, the rods having first ends which together define a first surface for shaping the beam around the beam axis and opposite ends from the first ends of the rods; a holder means with two spaced apart blocks mounted on the support plate, each block having axially aligned holes mounting the rods so that the first surface is defined and the beam is shaped by the first ends of the rods and at least one block being movable relative to the other block; releasable clamping means mounted on the support plate means and engaging the rods between the first and second ends to secure the rods together in the shape defined by the first ends of the rods, wherein the releasable clamping means includes the two spaced apart blocks and multiple coil spring means which have opposed ends which engage the blocks and which are positioned and mounted between the rods so that when at least one of the blocks is moved on the rods towards the other block the coil spring means is compressed and engages the rods surrounding the spring means to clamp the surrounding rods together and wherein the clamping means includes drive means mounted on the holder means and connected to at least one of the blocks for moving the blocks together to compress the coil spring against the rods to prevent movement of the rods in the holes in the blocks and for moving the blocks apart to release the spring means from the rods to allow movement of the rods in the holes in the blocks.

In particular the present invention relates to a collimator apparatus for producing a cross-sectionally shaped beam of radiation from a radiation source which comprises: support plate means having a central opening around a beam axis through which the beam of radiation can pass; a bundle of nested metal rods mounted adjacent the support plate means each rod having a longitudinal axis perpendicular to the beam axis and having first ends which together define a first surface for shaping the beam around the beam axis and opposite ends from the first ends; a holder means with two spaced apart blocks mounted adjacent the support plate means each block having axially aligned holes mounting the rods; rod shaping means adjacent the opposite ends of the rods, wherein the rod shaping means has a second surface corresponding to the first surface which defines varying positions of the first ends of the rods so that the first surface is defined and the beam is shaped by the first ends of the rods; and releasable clamping means engaging the blocks for securing the rods together in the shape defined by the shaping means, wherein the releasable clamping means includes the two spaced apart blocks and including multiple coil spring means which have opposed ends which engage the blocks and which are positioned and mounted between the rods so that when the blocks are moved on the rods towards each other the coil spring means are compressed and engage the rods surrounding each of the spring means to clamp the surrounding rods together and wherein the clamping means includes drive means mounted on the holder means and connected to one of the blocks for moving the blocks together to compress the coil spring means against the rods to prevent movement of the rods in the holes in the blocks and for moving the blocks apart to release the spring means from the rods to allow movement of the rods in the holes.

The present invention also relates to a method for producing a cross-sectionally shaped beam of radiation from a radiation source which comprises providing a collimator apparatus which comprises providing support plate means having a central opening around a beam axis through which the beam of radiation can pass; a bundle of nested rods mounted adjacent the support plate means each rod being movable into the beam at an angle to the beam axis to interfere with the beam, the rods having first ends which together define a first surface for shaping the beam around the beam axis and opposite ends from the first ends of the rods; a holder means with two spaced apart blocks mounted adjacent the support plate, each block having axially aligned holes mounting the rods so that the first surface is defined and the beam is shaped by the first ends of the rods; releasable clamping means mounted on the support plate means and engaging the blocks to secure the rods together in the shape defined by the first ends of the rods; moving the rods in the holes in the block to define the first surface; and clamping the rods with the releasable clamping means.

A primary improvement in the present invention is the use of a coil spring between rods to lock them in position. Also the single rapid reset of the rods without rotation of the position of the rods as described hereinafter is an improvement. The following specific description shows how this is accomplished.

SPECIFIC DESCRIPTION

FIGS. 1 to 5 show the improved collimator apparatus 10 of the present invention. Rods 11 and 11a are provided in bundles 12 and 12a parallel to axis a—a with one of the ends of the bundle 12 and 12a facing each other. The rods 11 and 11a are mounted through axially (a—a) aligned holes 14c (FIG. 5) in blocks 14 and 14a and are parallel to each other. The blocks 14 and 14a are mounted perpendicular to the rods 11 and 11a. The blocks 13 and 13a are parallel to blocks 14 and 14a and also have holes (not shown). The blocks 13, 13a, 14 and 14a are mounted on support plate 15 which has a rectangular opening 15a. The blocks 13 and 13a are U-shaped such that perpendicular legs 13b and 13c and 13d and 13e are facing each other in the plane of the rods 11 and 11a. Journal members 16 and 17 which are mounted on the outside of legs 13b and 13c are movable on spaced apart parallel slides 18 and 19. Support members 16a and 17a are secured to the support plate 15 and position the block 13a. Support plate 15 is bolted to a radiation source, e.g. a cyclotron or x-ray unit. The slides 18 and 19 are secured to the support member 15 by means of mounting members 20, 21, 22 and 23. The blocks 14 and 14a are each movable relative to the blocks 13 and 13a towards the respective legs 13b and 13c and 13d and 13e. The blocks 14 and 14a are guided for movement on pins 24 and 25 and 24a and 25a. The block 14 is moved by means of power cylinders 26 and 27 mounted inside journal members 16 and 17 adjacent legs 13b and 13c. The block 14a is moved by cylinders 26a and 27a mounted inside journal members 16a and 17a. Each cylinder 26, 26a, 27 and 27a has an arm 28 or 28a which is connected to the blocks 14 or 14a to provide the movement. Movement of the arms 28 or 28a towards the cylinder 26 and 27 or 26a and 27a moves the blocks 14 and 14a towards the block 13 or 13a along the rods 11 or 11a. As will be seen hereinafter, this construction provides a means for clamping the rods 11 and 11a in a predetermined position.

Figure 1:
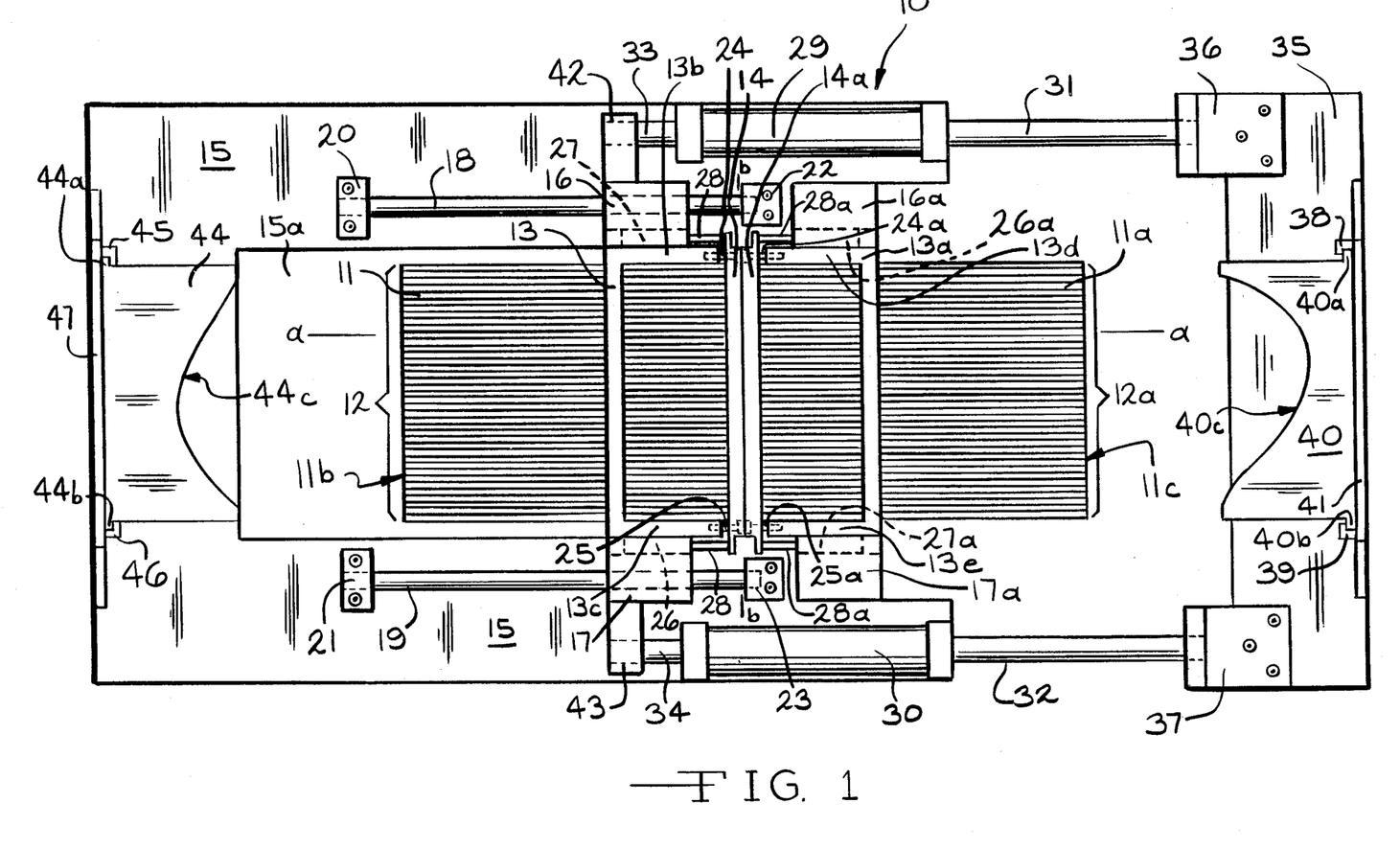
FIG. 1 is a plan view of the collimator apparatus 10 of the present invention, particularly illustrating nested rods 11 and 11a moved together without defining an opening for the radiation.
Figures 2, 3, 4, 5:
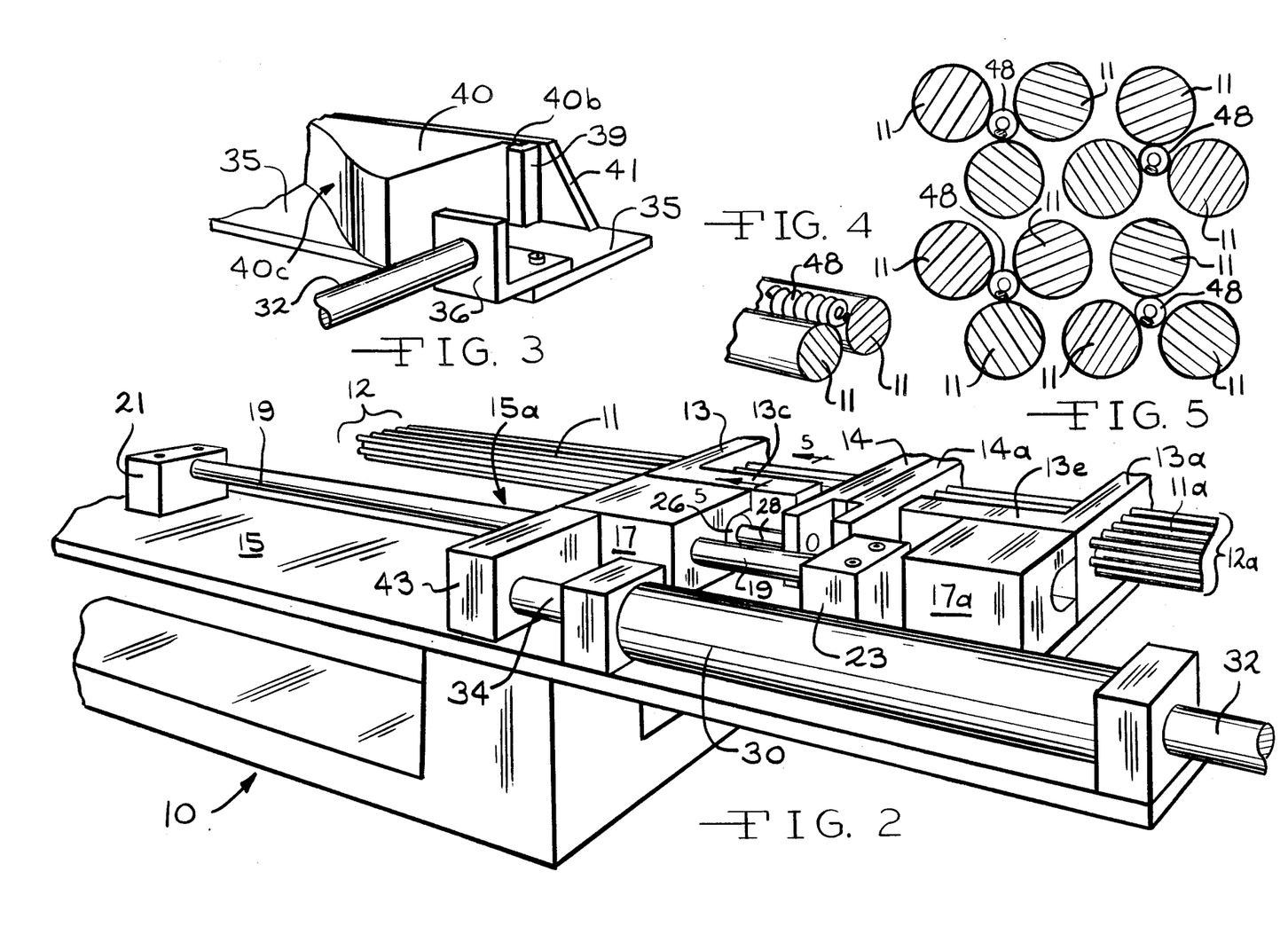

Movement of the bundle 12 and 12a of rods 11 and 11a is accomplished by means of cylinders 29 and 30 mounted on support member 15 using arms 31 and 32 and 33 and 34. The distal ends of the arms 31 and 32 are secured to a movable end plate 35 by means of brackets 36 and 37. A pair of spaced apart slotted blocks 38 and 39 are mounted on a backing plate 41 and support a shaping member 40 which has two projections 40a and 40b which slide into slotted blocks 38 and 39. The arms 33 and 34 are mounted on extensions 42 and 43 from journal members 16 and 17. Thus as can be seen the blocks 13 and 14 supporting rods 11 as bundles 12 move as a unit along with journaled members 16 and 17, extensions 42 and 43, arms 31, 32, 33 and 34 and end plate 35.

Opposite the shaping member 40 is a second shaping member 44 mounted by second slotted blocks 45 and 46 mounted on a second backing plate 47. Projections 44a and 44b slide into sloted blocks 45 and 46. Each of the shaping members 40 and 44 has a surface 40c or 44c which faces the ends 11b and 11c of the bundles 12 and 12a respectively. Movement of the bundles 12 and 12a of rods 11 and 11a so that the ends 11b and 11c encounter the surfaces 40c and 44c defines and shapes an opening (see opening 111 in FIG. 9).

As shown in FIGS. 4 and 5 a spring 48 is provided in between each set of three rods 11 (and 11a) such that each rod is in contact with a spring 48. The spring 48 extends between blocks 13 and 14 (and between blocks 13a and 14a) in its uncompressed form such that the springs 48 can then be compressed by the blocks 13 and 14 or 13a and 14a. Upon movement of the block 14 towards arms 13b and 13c by cylinders 26 and 27, each spring 48 is compressed and expands and bends to fill the void between the three rods 11 thus locking the rods 11 in position on the blocks 13 and 14. In a similar manner the rods 11a are locked by blocks 13a and 14a. Thus the springs 48 provide a unique one step sequence for locking the rods 11 and 11a in position.

FIGS. 6 to 9 show step by step views of the operation of a collimator apparatus 100 similar to the apparatus 10 shown in FIG. 1. The support plate 15 does not have to be rotated to position the rod 101 and 101a and bundles 102 and 102a as in the collimator apparatus shown in Ser. No. 850,486 referred to above. As can be seen from FIGS. 6 to 9, the right hand block 104a remains fixed along line b—b. As in FIGS. 1 to 5, rods 101 and 101a are in bundles 102 and 102a and secured by blocks 103 and 104 and 103a and 104a and by springs 48 (such as shown in FIGS. 4 and 5). The blocks 103 and 104 (or 103a or 104a) are moved together by means of cylinders 105 and 106 or 105a and 106a using arms 107 and 107a. The blocks 104 and 104a are movably secured to blocks 103 and 103a by means of pins 108 or 108a. The blocks 103 and 104 are moved along axis c—c by extension 109. Attached to each extension 109 and 109a are shaping members 110 and 110a with inner surfaces 110b and 110c which face the bundle of rods 102 and 102a.

Figure 7:
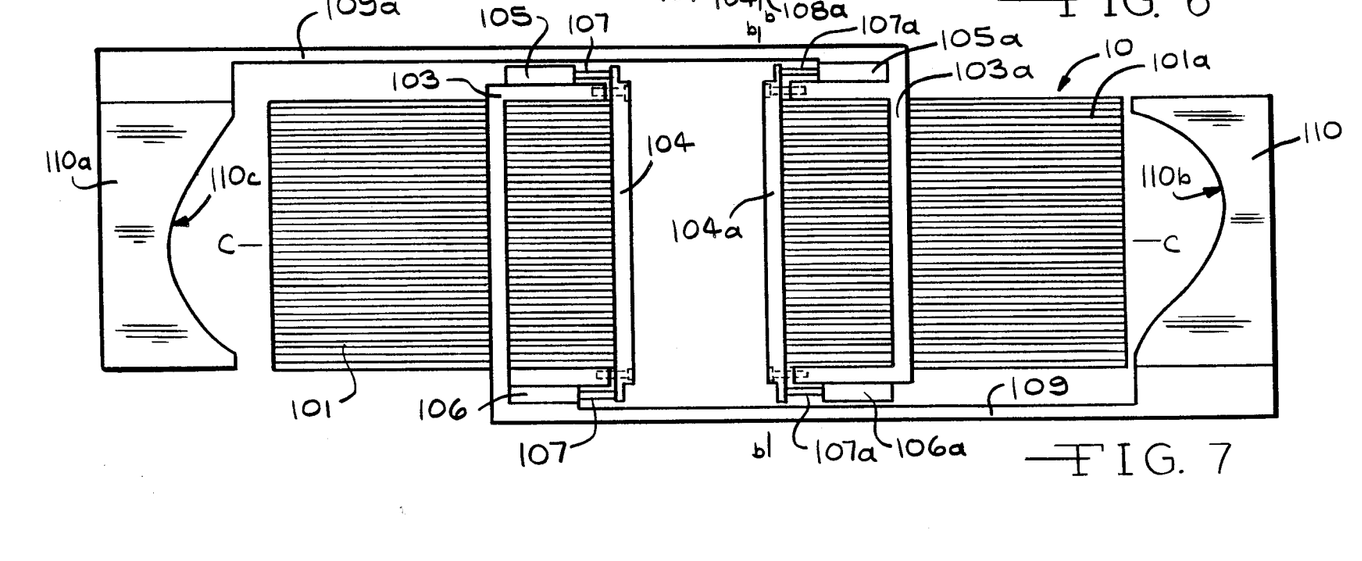
Figure 8:
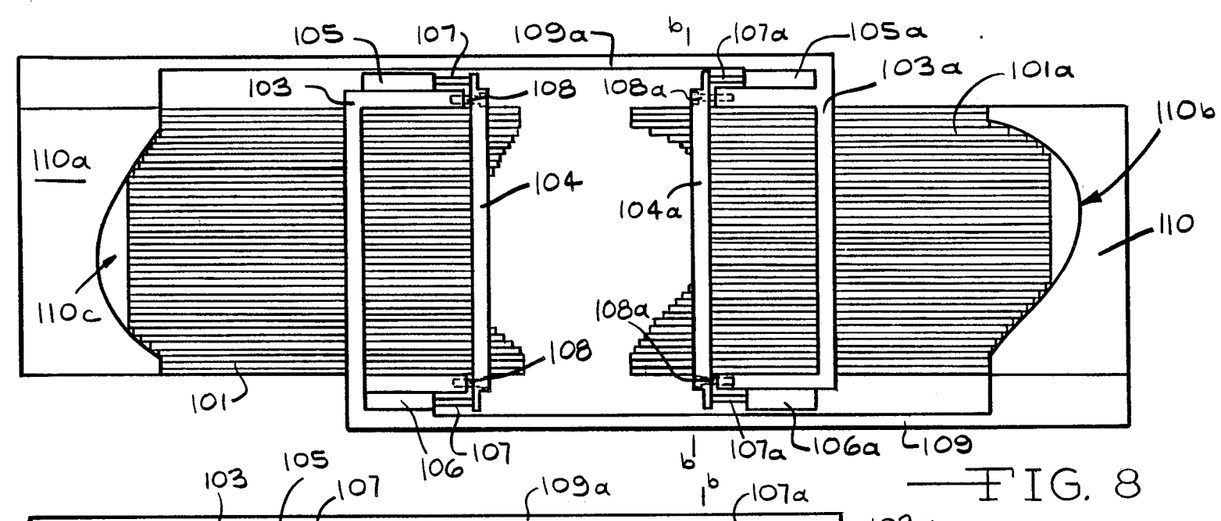
Figure 9:
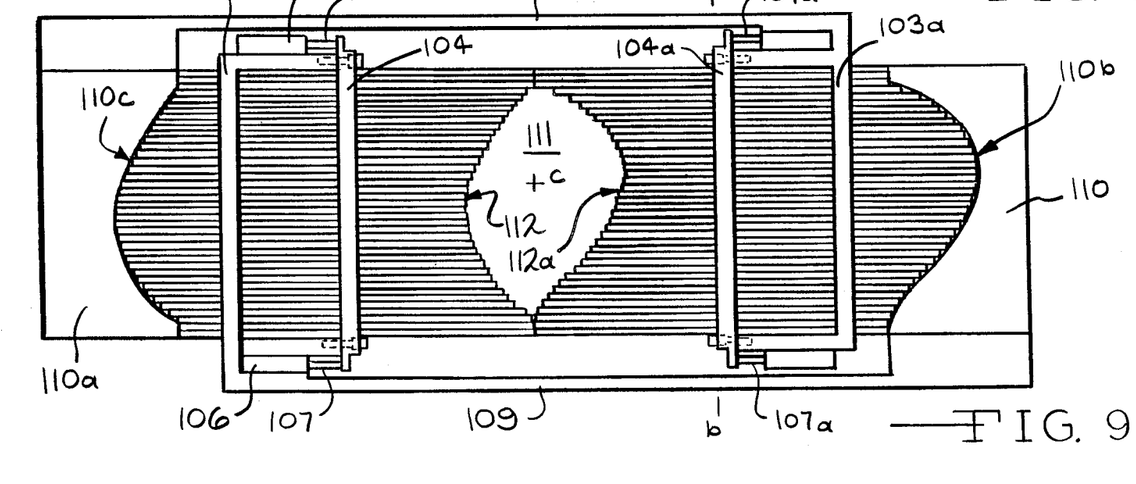

As shown in FIGS. 7 and 8, the rods 101 are moved towards the surfaces 110c of the respective shaping member 110a. At the same time, surface 110b of shaping member 110 moves towards rods 101a. The ends of the rods 101 and 101a conform to the shaping members 110 and 110a by moving extension 109 towards shaping member 110a. As shown in FIG. 9, the blocks 103 and 104 and 103a and 104a are then moved together and the rods 101 and 101a are clamped in position after the opening 111 is formed.

As can be seen from FIGS. 6 to 9, the extension 109 moves shaping member 110 into rods 101a. The blocks 103 and 104 on the extension 109 moves the rods 101 into shaping member 110a. Thus the opening 111 is defined by movement of the bundles 102 and 102a of rods 101 and 101a against the shaping members 110 and 110a.

Figure 6:
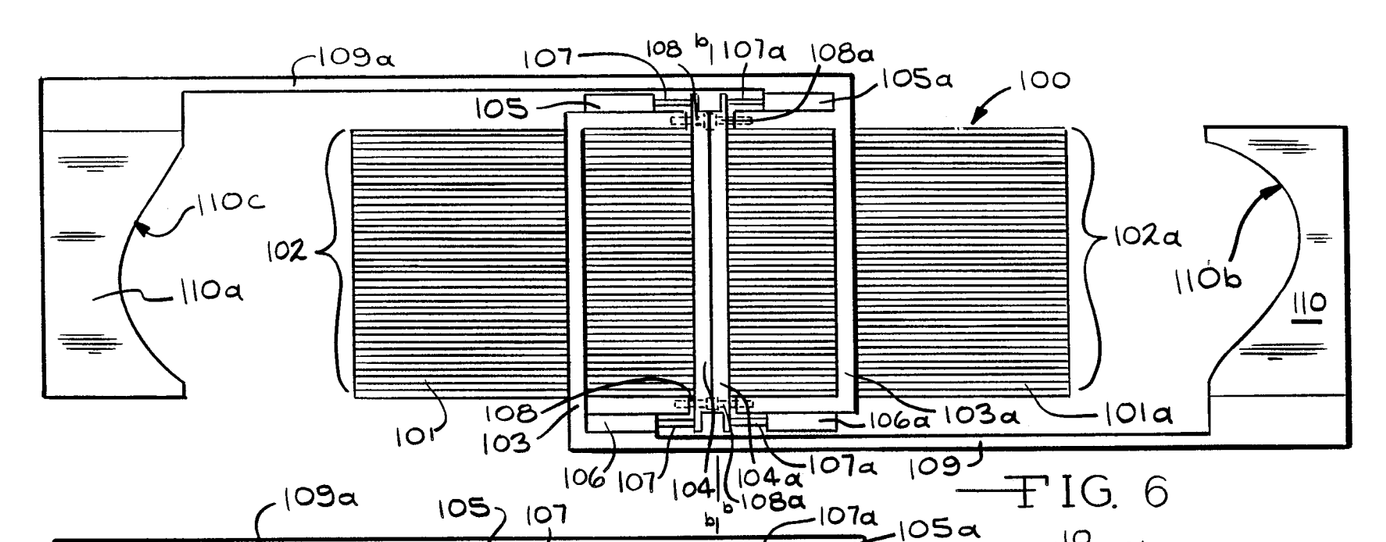

The rods 101 and 101a in bundles 102 and 102a preferably have longitudinal axes which are offset from each other about ½ a rod diameter. This prevents abutting rods 101 or 101a from being pushed through the blocks 104 or 104a during resetting to the position as shown in FIG. 6. This is accomplished by moving the extension 109 to the right as shown in the drawing so that the rods are all in the FIG. 6 position as a preliminary step to reforming a new opening 111.

As used herein the term "nested" means that the rods which define the first surface or opening are close to each other preferably on a spacing between the rods of no more than about 0.2 mm. Circular cross-sectioned rods 11 and 11a or 101 and 101a are preferred in order to provide ease of machining of the holes in blocks 13, 14, 13a and 14a or 103, 103a, 104 and 104a. The rods preferably have a cross-section between about 3 and 5 mm. The rods can also have a polygonal cross-section. The rods are generally made of tungsten or stainless steel but other materials with good radiation absorption characteristics can also be used.

The rod shaping member 40, 44 or 110 and 110a is preferably composed of polystyrene because it is easily cut into a desired shape of the surface 40c, 44c, or 110b, 110c using a hot wire or the like. Other materials can be used so long as they can be shaped.

Figure 10:
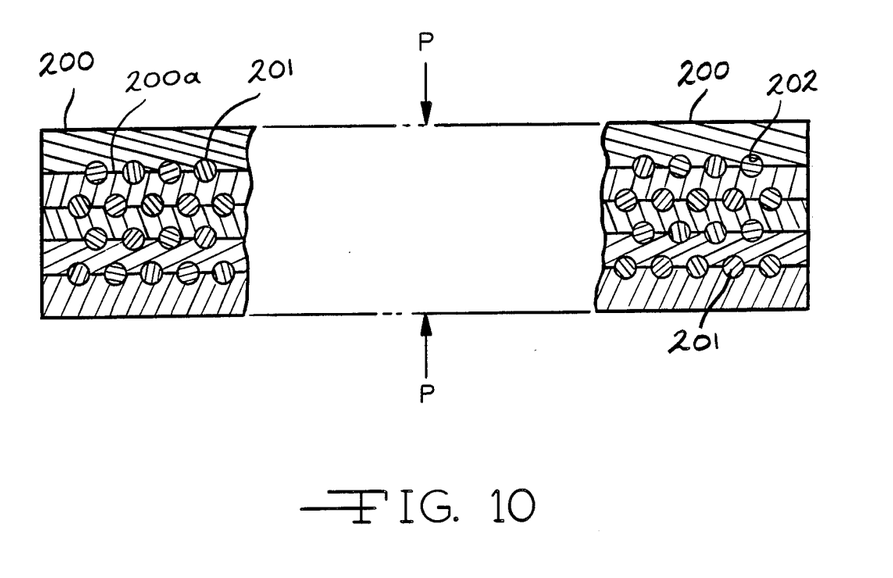
FIG. 10 shows a different block 200 for clamping rods 201 in holes 202.

FIG. 10 shows an alternative block 200 for securing rods 201 in holes 202. The block 200 has spaces 200a between the rods 201 such that pressure P applied to the block 200 produces clamping. This releasable clamping means is not as reliable as that of FIGS. 1 to 9.

As will be apparent, the rods 11 or 11a and 101 and 101a can be moved into position by any means. A shaping member (not shown) defining the shape of the opening 111 as described in Ser. No. 850,486 can be used. It is intended that the foregoing description be only illustrative of the present invention.

We claim:

1. A collimator apparatus for producing a cross-sectionally shaped beam of radiation from a radiation source which comprises:
   (a) support plate means having a central opening around a beam axis through which the beam of radiation can pass;
   (b) a bundle of nested rods mounted adjacent the support plate means each rod being movable into the beam at an angle to the beam axis to interfere with the beam, the rods having first ends which together define a first surface for shaping the beam around the beam axis and opposite second ends from the first ends of the rods;
   (c) a holder means including spaced apart blocks mounted on the support plate, each block having axially aligned holes mounting the rods so that the first surface is defined and the beam is shaped by the first ends of the rods; and
   (d) releasable clamping means for moving the blocks so that the blocks or means between the blocks adjacent the rods are in engagement with the rods to secure the rods together in the shape defined by the first ends of the rods.

2. The apparatus of claim 1 wherein the blocks can be compressed together around the rods by the clamping means to reduce the diameter of the holes and thus secure the rods together.

3. The apparatus of claim 1 wherein coil springs are provided between the rods and blocks which can be compressed by moving the blocks along the rods towards each other to hold the rods in position and can be uncompressed to release the rods.

4. A collimator apparatus for producing a cross-sectionally shaped beam of radiation from a radiation source which comprises:

(a) support plate means having a central opening around a beam axis through which the beam of radiation can pass;

(b) a bundle of nested rods mounted adjacent the support plate means each rod being movable into the beam at an angle to the beam axis to interfere with the beam, the rods having first ends which together define a first surface for shaping the beam around the beam axis and opposite second ends from the first ends of the rods;

(c) a holder means with two spaced apart blocks mounted on the support plate, each block having axially aligned holes mounting the rods so that the first surface is defined and the beam is shaped by the first ends of the rods and at least one block being movable relative to the other block;

(d) releasable clamping means mounted on the support plate means and engaging the blocks and rods between the first and second ends to secure the rods together in the shape defined by the first ends of the rods, wherein the releasable clamping means includes multiple coil spring means which have opposed ends which engage the blocks and which are positioned and mounted between the rods so that when at least one of the blocks is moved on the rods towards the other block and coil spring means is compressed and engages the rods surrounding the spring means to clamp the surrounding rods together and wherein the clamping means includes drive means mounted on the holder means and connected to at least one of the blocks for moving the blocks together to compress the coil spring against the rods to prevent movement of the rods in the holes in the blocks and for moving the blocks apart to release the spring means from the rods to allow movement of the rods in the holes in the blocks.

5. The collimator apparatus of claim 4 wherein there are two opposed bundles of rods mounted on the support plate means with the first ends opposite each other and axially displaced relative to each other.

6. The collimator apparatus of claim 4 wherein the rods are circular in cross-section and have a diameter of between about 1 mm and 10 mm.

7. The collimator apparatus of claim 4 wherein rods have a composition for interfering with a neutron beam.

8. The collimator apparatus of claim 4 wherein the rods have a composition for interference with a photon beam.

9. A collimator apparatus for producing a cross-sectionally shaped beam of radiation from a radiation source which comprises:

(a) support plate means having a central opening around a beam axis through which the beam of radiation can pass;

(b) a bundle of nested metal rods mounted adjacent the support plate means each rod having a longitudinal axis perpendicular to the beam axis and having first ends which together define a first surface for shaping the beam around the beam axis and opposite second ends from the first ends;

(c) a holder means with two spaced apart blocks mounted adjacent the support plate means each block having axially aligned holes mounting the rods;

(d) rod shaping means adjacent the opposite second ends of the rods, wherein the rod shaping means has a second surface corresponding to the first surface which defines varying positions of the first ends of the rods so that the first surface is defined and the beam is shaped by the first ends of the rods; and (e) releasable clamping means engaging the blocks for securing the rods together in the shape defined by the shaping means, wherein the releasable clamping means includes multiple coil spring means which have opposed ends which engage the blocks and which are positioned and mounted between the rods so that when the blocks are moved on the rods towards each other the coil spring means are compressed and engage the rods surrounding each of the spring means to clamp the surrounding rods together and wherein the clamping means includes drive means mounted on the holder means and connected to one of the blocks for moving the blocks together to compress the coil spring means against the rods to prevent movement of the rods in the holes in the blocks and for moving the blocks apart to release the spring means from the rods to allow movement of the rods in the holes.

10. The collimator apparatus of claim 9 wherein there are two opposed bundles of rods mounted on the support plate means with the first ends opposite each other and with the opposed rods having parallel longitudinal axis offset from each other on the axis.

11. The collimator apparatus of claim 9 wherein the rods are circular in cross-section and have a diameter of between about 1 mm and 10 mm.

12. The collimator apparatus of claim 9 wherein the metal composition of the rods is selected from the group consisting of tungsten and stainless steel.

13. The collimator apparatus of claim 9 wherein the rod shaping means is composed of polystyrene foam which is mounted on the holder means.

14. The collimator apparatus of claim 9 wherein the rods have a composition for interference with a neutron or photon beam.

15. The collimator apparatus of claim 9 wherein the rods have a polygonal cross-section.

16. The collimator apparatus of claim 9 wherein the rods have a circular cross-section and wherein the rod shaping means is composed of a polystyrene foam.

17. The apparatus of claim 9 wherein there are two opposed bundles of rods and blocks mounted on the support plate means with the first ends opposite each other and with the opposed rods having parallel longitudinal axis and wherein one bundle of rods and blocks is movable relative to the other bundle of rods and blocks so that the bundle of rods is shaped by a first shaping means, and wherein a second rod shaping means is movable with the movable bundle of rods and blocks to engage the opposite ends of the rods so that the first surfaces are defined and wherein motive means is provided on the support plate means to move the movable bundle of rods, and blocks and second rod shaping means.

18. The apparatus of claim 17 wherein the movable bundle of rods, blocks and shaping means are moved by an arm of a hydraulic or pneumatic cylinder as the motive means which is mounted on the support plate means.

19. The method for producing a cross-sectionally shaped beam of radiation from a radiation source which comprises:

(a) providing a collimator apparatus which comprises support plate means having a central opening around a beam axis through which the beam of radiation can pass; a bundle of nested rods mounted adjacent the support plate means each rod being movable into the beam at an angle to the beam axis to interfere with the beam, the rods having first ends which together define a first surface for shaping the beam around the beam axis and opposite second ends from the first ends of the rods; a holder means including spaced apart blocks mounted on the support plate, each block having axially aligned holes mounting the rods so that the first surface is defined and the beam is shaped by the first ends of the rods and at least one block being movable relative to the other block; releasable clamping means engaging the rods between the first and second ends to secure the rods together in the shape defined by the first ends of the rods, wherein the releasable clamping means includes multiple coil spring means which have opposed ends which engage the blocks and which are positioned and mounted between the rods so that when at least one of the blocks is moved on the rods towards the other block the coil spring means is compressed and engages the rods surrounding the spring means to clamp the surrounding rods together and wherein the clamping means includes drive means mounted on the holder means and connected to one of the blocks for moving the blocks together to compress the coil spring against the rods to prevent movement of the rods in the holes in the blocks and for moving the blocks apart to release the spring means from the rods to allow movement of the rods in the holes in the blocks;

(b) moving the rods in the holes in the blocks so that the rods define the first surface;

(c) clamping the rods with the releasable clamping means by moving the blocks so that the spring means is compressed to prevent movement of the rods; and (d) producing the shaped beam defined by the first ends of the rods.

20. The method for producing a cross-sectionally shaped beam of radiation from a radiation source which comprises:

(a) providing a collimator apparatus which comprises support plate means having a central opening around a beam axis through which the beam of radiation can pass; a bundle of nested metal rods mounted on the support plate means each rod having a longitudinal axis perpendicular to the beam axis and having first ends which together define a first surface for shaping the beam around the beam axis and opposite second ends from the first ends; a holder means with two spaced apart blocks mounted on the support plate each block having axially aligned holes mounting the rods; rod shaping means adjacent the opposite second ends of the rods, wherein the rod shaping means has a second surface corresponding to the first surface which defines varying positions of the first ends of the rods so that the first surface is defined and the beam is shaped by the first ends of the rods; and releasable clamping means for securing the rods together in the shape defined by the shaping means, wherein the releasable clamping means includes multiple coil spring means which have opposed ends which engage the blocks and which are positioned and mounted between the rods so that when the blocks are moved on the rods towards each other the coil spring means is compressed and engages the rods surrounding the spring means to clamp the surrounding rods together and wherein the clamping means includes drive means mounted on the holder means and connected to at least one of the blocks for moving the blocks together to compress the coil spring against the rods to prevent movement of the rods in the holes in the blocks and for moving the blocks apart to release the spring means from the rods to allow movement of the rods in the holes;

(b) moving the opposite rods in the holes in the blocks with the second ends against the rod shaping means to define the first surface;

(c) clamping the rods with the releasable clamping means by moving the blocks so that the spring means is compressed to prevent movement of the rods; and (d) producing the shaped beam defined by the first ends of the rods.

21. The method of claim 20 wherein there are two bundles of rods and blocks each with a rod shaping means mounted on the support plate means with the first ends opposite each other and with the opposed rods having parallel longitudinal axis offset from each other wherein one bundle of rods and blocks are movable together relative to the other bundle of rods and blocks and wherein one bundle of rods and blocks is moved relative to the other bundle of rods and blocks so that the one bundle of rods is shaped by a first of the shaping means and wherein a second rod shaping means is moved with the movable bundle of rods so that the opposite second ends of the rods in the other bundle of rods engages a second of the rod shaping means so that the first surfaces are defined for each of the bundles of rods and wherein motive means mounted on the support plate means moves the second bundle of rods and blocks and second rod shaping means together and wherein the bundles of rods are secured together by the clamping means when each of the first surfaces are defined by the first ends of the rods.

22. The method for producing a cross-sectionally shaped beam of radiation from a radiation source which comprises:

(a) providing a collimator apparatus for producing a cross-sectionally shaped beam of radiation from a radiation source which comprises: support plate means having a central opening around a beam axis through which the beam of radiation can pass; a bundle of nested rods mounted adjacent the support plate means each rod being movable into the beam at an angle to the beam axis to interfere with the beam, the rods having first ends which together define a first surface for shaping the beam around the beam axis and opposite second ends from the first ends of the rods; a holder means including spaced apart blocks mounted adjacent the support plate, each block having axially aligned holes mounting the rods so that the first surface is defined and the beam is shaped by the first ends of the rods; releasable clamping means for moving the blocks so that the blocks or means between the blocks adjacent the rods are in engagement with the rods to secure the rods together in the shape defined by the first ends of the rods;

(b) moving the rods in the holes in the block so that the rods define the first surface;

(c) clamping the rods with the releasable clamping means by moving the blocks to prevent movement of the rods; and (d) producing the shaped beam defined by the first ends of the rods.

* * * * *

UNITED STATES PATENT AND TRADEMARK OFFICE
CERTIFICATE OF CORRECTION

PATENT NO. : 4,739,173
DATED : April 19, 1988
INVENTOR(S) : Gabe F. Blosser, Emanuel B. Jemison, Henry G. Blosser, and Richard L. Maughan It is certified that error appears in the above—identified patent and that said Letters Patent is hereby corrected as shown below:

Column 1, line 41 "with" should be --which--.

Column 2, line 1 "apparant" should be --apparent--.

Column 5, line 7 "sloted" should be --slotted--.

Column 7, line 26 "and" should be --the--.

Signed and Sealed this

Twenty-seventh Day of September, 1988

Attest:

DONALD J. QUIGG

*Attesting Officer*  *Commissioner of Patents and Trademarks*